United States Patent [19]

Takeda et al.

[11] Patent Number: 4,584,010
[45] Date of Patent: Apr. 22, 1986

[54] METHOD FOR CONTROLLING WEEDS IN PADDY RICE

[75] Inventors: Shunji Takeda, Yokohama, Japan; Takeshi Yuyama, Wilmington, Del.

[73] Assignee: E. I. Du Pont de Nemours and Company, Wilmington, Del.

[21] Appl. No.: 547,974

[22] Filed: Nov. 2, 1983

[51] Int. Cl.⁴ .................. A01N 43/48; A01N 43/40; A01N 37/00
[52] U.S. Cl. ........................... 71/92; 71/94; 71/100
[58] Field of Search ..................... 71/92, 94, 100

[56] References Cited

U.S. PATENT DOCUMENTS

| | | | |
|---|---|---|---|
| 3,682,616 | 8/1972 | Kimura et al. | 71/93 |
| 3,746,532 | 7/1973 | Kimura et al. | 71/100 |
| 3,929,452 | 12/1975 | Kimura et al. | 71/100 |
| 4,260,824 | 4/1981 | Gaughan | 71/100 |
| 4,272,283 | 6/1981 | Takematsu et al. | 71/94 |
| 4,343,737 | 8/1982 | Konno et al. | 260/239 BF |
| 4,420,325 | 12/1983 | Sauers | 71/92 |

FOREIGN PATENT DOCUMENTS 0051466  5/1982  European Pat. Off. .

OTHER PUBLICATIONS

Takematsu et al, I, "Herbicides" Japan, Kokai, 76, 98,331, 8 pages, Aug. 30 (1976).

Primary Examiner—Glennon H. Hollrah
Assistant Examiner—Andrew Duff Meikle

[57] ABSTRACT

A method for controlling weeds in Japonica rice paddy fields comprising applying an herbicidally effective amount of the compound methyl 2-[((4,6-dimethoxypyrimidin-2-yl)aminocarbonyl)aminosulfonyl]methyl benzoate in combination with a compound selected from 5-(4-chlorobenzyl)-N,N-diethylthiolcarbamate and S-(1-methyl-1-phenethyl)-piperidine-1-carbothioate.

13 Claims, No Drawings

METHOD FOR CONTROLLING WEEDS IN PADDY RICE

BACKGROUND OF THE INVENTION

This invention relates to a method of controlling weeds in Japonica rice paddy fields and to herbicidal compositions useful for that purpose.

Rice satisfies the food needs of a large portion of the world's population. The current population explosion and concomitant food shortage underlie the need for improvements in the efficiency of producing rice. One such improvement being sought in an efficient method for controlling weeds in rice paddies.

The compound methyl 2-[(((4,6-dimethoxypyrimidin-2-yl)aminocarbonyl)aminosulfonyl]methyl benzoate

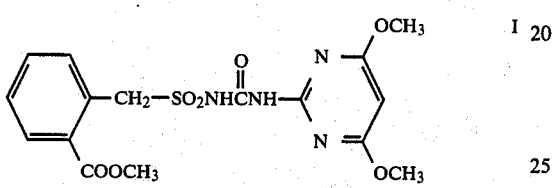

has been found to be very effective for controlling both annual and perennial paddy field weeds which commonly plague rice paddies. This compound (Compound I) and a method of preparing it are disclosed in European Patent Application No. 81305160.4 (Publication No. 51466, published May 12, 1982). Although the test results in the European Application (Test E) indicate that Compound I (referred to therein as Compound 6) does not cause phytotoxicity to rice, later tests have shown that, although the compound causes little or no phytotoxicity to Indica rice plants, it causes marked phytotoxicity to Japonica rice plants even at low application rates. Thus, even though Compound I was effective in controlling paddy field weeds at very low, environmentally safe application rates, its use as a herbicide in Japonica rice was severely limited.

SUMMARY OF THE INVENTION

It has now been found that weeds in Japonica rice paddy fields can be controlled without causing unacceptable phytotoxicity to the rice plants by combining application of Compound I with application of at least one compound selected from S-(4-chlorobenzyl)N,N-diethylthiocarbamate (Compound II) and S-(1-methyl1-phenethyl)-piperidine-1-carbothioate (Compound III). The latter two compounds are known to possess herbicidal activity, but, surprisingly, it has been found that, when they are used in conjunction with Compound I to control weeds in Japonica rice paddy fields, the degree of phytotoxicity to the rice plants is greatly reduced. This invention therefore relates to a method for controlling weeds in paddy fields of Japonica rice comprising applying to the locus of said weeds a herbicidally effective amount of Compound I and an antidotally effective amount of a compound selected from Compounds II and III. This invention also relates to a herbicidal composition comprising as active ingredients a herbicidally effective amount of Compound I and an antidotally effective amount of one of Compounds II and III.

DETAILED DESCRIPTION OF THE INVENTION

The compound S-(4-chlorobenzyl)-N,N-diethylthiocarbamate

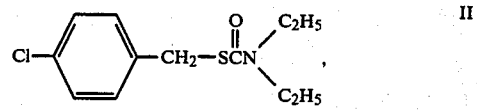

is a commercially available herbicide. Sold under the trademarks Bolero ® (Chevron Chemical Co.) and Saturn ® (Kumiai Chemical Industry Co., Ltd.), it is also described in U.S. Pat. No. 3,682,616. The compound S-(1-methyl-1-phenethyl)-piperidine-1-carbothioate

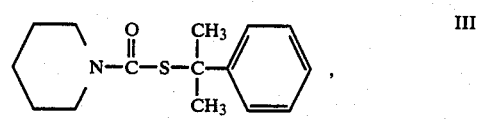

its herbicidal utility, and a method for preparing it are disclosed in U.S. Pat. No. 4,343,737.

According to the method of this invention, it is preferred to apply Compound I in combination with Compound II or III to the water surface in the paddy field in water-filled condition in a season of about 1 to about 15 days, more preferably about 2 to about 14 days, after transplantation of Japonica rice plant seedlings therein. The optimal timing and method of application could be selected based on the location of the paddy, the variety of Japonica rice plant, and the kind and growth condition of the weeds to be controlled. Spraying immediately before or after transplantation, however, adversely affects young rice plants, and, of course, too long of a delay in spraying lowers the level of control of the weeds.

When applying the compounds to the water surface of the paddy, it is convenient to spray them over the paddy fields in which the Japonica rice plant seedlings have been transplanted, and it is not necessary to avoid their adhering to some extent to the leaf surfaces of the rice plant seedlings. It is most convenient to apply the compounds in combination in a form of a preformulated composite herbicide, but if desired, single agents of the compound of Formula I and a compound of Formula II or III may be mixed on the spot for their joint application, or otherwise, they may be applied sequentially.

A herbicidally effective amount of Compound I will generally fall within the range of about 65 to 120 g/ha, preferably about 70 to 110 g/ha, and more preferably about 75 to 100 g/ha. What encompasses a herbicidally effective amount of the compound will, of course, vary according to the condition of the field soil, weather conditions, location, and others. Compound I will generally be used in combination with Compound II in a weight ratio of 1:about 20 to 50 and in combination with Compound III in a weight ratio of 1:about 10 to 50. When used in these proportions, Compounds II and III serve to reduce phytotoxicity to the rice caused by Compound I, i.e., they exert an antidotal effect.

Examples of weeds that can be controlled according to this invention include perennial field weeds such as *Sagittaria pygmaea, Sagittaria trifolia, Scirpus hotarui,*

*Cyperus serotinus, Eleocharis acicularis* and *Eleocharis kuroguwai.* Also controlled are annual field weeds such as *Ec, Cyperus difformis, Monochoria vaginalis, Rotala indica, Lindernia procubens, Dopatrium junceum,* and *Elatine triandra.*

A wide variety of Japonica rice plants are known, for example, KOSHIHIKARI, NISHIHOMARE, SETOHOMARE, KITAHIKARI, SASANISHIKI, and NIHONBARE.

This invention is further illustrated by the following examples.

EXAMPLE 1

Phytotoxicity Caused by Compound I on Japonica vs. Indica Rice

Paddy field soil in a wagner pot with 1/5000 are was watered, fertilized and tilled. Three varieties of rice plant seeds:
Indica: IR-24
Indica: RP-93
Japonica: NIHONBARE
were subjected to emergence promoting treatment and then directly sowed at water-filled conditions. The surface water of the field was held at 2–3 cm in depth during the test season. The chemical was applied to the water surface in the 0.5 to 1 leaf season or 1.5 to 2 leaf season of the rice plants, respectively, in dosages indicated in Table I. Investigations were made 17 days after treatment. Evaluations were made using the following ten grade system and are presented in Table 1.
(Phytotoxicity)

0—Growth was not affected
1—Growth was inhibited insignificantly in plant length and tiller
2—Growth was inhibited slightly in plant length and tiller
3—Growth was inhibited considerably in plant length and tiller
4—Growth was inhibited obviously in plant length and tiller
5—Growth was inhibited in plant length and filler, yellowed considerably
6—Growth was inhibited in plant length and filler, yellowed obviously
7—Growth was inhibited in plant length and filler, yellowed markedly
8—Inhibited markedly in plant length and inhibited markedly in tiller
9—Nearly withered
10—Completely withered In the case where the assessment is in excess of about 2.5, substantially phytotoxicity occurs, and an assessment of 3 or more is considered to be not practical.

TABLE 1

| Test Chemical | Application rate (g/ha) | Application season Leaf age | Assessment (phytotoxicity) Indica IR-24 | Indica RP-93 | Japonica NIHON-BARE |
|---|---|---|---|---|---|
| Compound I | 50 | (0.5 | 1 | 2 | 5 |
|  | 100 | ~1) | 3 | 3.5 | 6 |
|  | 150 |  | 4 | 4.5 | 7 |
| Control (untreated) | — |  | 0 | 0 | 0 |
| Compound I | 50 | (1.5 | 0.5 | 0.5 | 3 |
|  | 100 | ~2) | 1.5 | 1.5 | 3.5 |
|  | 150 |  | 2 | 2 | 4.5 |
| Control | — |  |  |  |  |

TABLE 1-continued

| Test Chemical | Application rate (g/ha) | Application season Leaf age | Assessment (phytotoxicity) Indica IR-24 | Indica RP-93 | Japonica NIHON-BARE |
|---|---|---|---|---|---|
| (untreated) |  |  |  |  |  |

These data show that Compound I surprisingly causes unacceptable phytotoxicity to Japonica rice, even at application rates as low as 50 g/ha, while causing far less phytotoxicity to the Indica varieties.

EXAMPLE 2

Antidoting Activity of Compound II - Pot Test

Standard tests were made with addition of water-leakage conditions of 2 cm/8 hours daily using a wagner pot with 1/5000 are. Seedlings of 2.5 leaved Japonica rice plant NIHONBARE raised in a seedling growing box were transplanted into the pot. Chemical treatment was effected one day after transplantation in application rates indicated in the following table. During the test season water depth was held at 3 mm at the above water-leaking conditions. Observations and investigations were made 13 days and 20 days after the chemical application and are reported in Table 2. Evaluations were made according to the scale described in Example 1.

TABLE 2

| Chemical | Application rate (g/ha) | Assessment (rice phytotoxicity) After 13 days | After 20 days | Rice Growth condition* (%) Stalk number | Plant length | Dry weight of ground part |
|---|---|---|---|---|---|---|
| Compound I | 100 | 3.5 | 4 | 91 | 100 | 82 |
| Compound I + Compound II | 100 + 3000 | 2 | 2 | 99 | 101 | 98 |
| Compound II | 3000 | 0 | 0 | 109 | 99 | 106 |
| Control (untreated) | — | 0 | 0 | 100 | 100 | 100 |

*Indicated in percentages (%) based on the stalk number, plant length and dry weight of ground part in Control.

EXAMPLE 3

Antidoting Activity of Compound II - Field Test

Field tests under natural conditions were conducted in paddy fields in eight different locations in Japan (four in the northern part and four in the southern part). Seedlings of Japonica rice plant, NIHONBARE, 2.2 to 2.5 of leaf age, were transplanted, respectively, by rice planter or by hand in paddy fields after breaking land, watering, fertilizing, plowing and leveling according to customary practice. After transplantation the surface water of the paddy field was held in condition where water was filled in a depth of 3 to 5 cm. The chemicals shown in Table 3 were applied to the water surface 3–11 days after transplantation. Testing was made in 6–10 m² for every area, respectively in the double system. Table 3 shows results of observations made 15–25 days after the chemical application. Results are indicated as average values (rounded off) of test results in the 8 different places. Assessment of phytotoxicity is the same as described in Example 1. Herbicidal effect was assessed as follows.

(Herbicidal effect)

0 —90% or more of weed amounts of Control (untreated area) survived.
1—From 80% to less than 90% of Control (untreated area) survived.
2—From 70% to less than 80% of Control (untreated area survived.
3—From 60% to less than 70% of Control (untreated area) survived.
4—From 50% to less than 60% of Control (untreated area) survived.
5—From 40% to less than 50% of Control (untreated area) survived.
6—From 30% to less than 40% of Control (untreated area) survived.
7—From 20% to less than 30% of Control (untreated area) survived.
8—From 10% to less than 20% of Control (untreated area) survived.
9—From 10% to 0% of Control (untreated area) survived.

Further, in the Table, weed symbols are as follows:
Ec: TAINUBIE
Mv: *Monochoria vaginalis*
Bl: Other annual broadleaved weeds (such as *Rotala indica, Lindernia procubens, Elatine triandra* and so on)
Ea: *Eleocharis acicularis*
Sh: *Scirpus hotarui*
Sp: *Sagittaria pygmaea*
Ac: *Alisma plantago-aquatica*
Cs: *Cyperus serotinus*

TABLE 3

| Chemical | Application rate (g/ha) | Herbicidal Effect | | | | | | | | Phytotoxicity to rice |
|---|---|---|---|---|---|---|---|---|---|---|
| | | Annual field weeds | | | Perennial field weeds | | | | | |
| | | Ec | Mv | Bl | Ea | Sh | Sp | Ac | Cs | |
| Compound I | 75 | 5 | 10 | 10 | 10 | 9 | 9 | 8.5 | 9 | 3.5 |
| | 100 | 6 | 10 | 10 | 10 | 9.5 | 9.5 | 9 | 9 | 4.4 |
| Compound I + Compound III | 75 + 2100 | 9 | 9.5 | 9.5 | 10 | 9 | 9 | 9 | 9 | 0.9 |
| Compound I + Compound II | 100 + 2800 | 9.5 | 10 | 10 | 10 | 9.5 | 9.5 | 9 | 9.5 | 1.3 |
| Compound II | 2100 | 10 | 7 | 8 | 10 | 8 | 3 | 3 | 7 | 0 |
| | 2800 | 10 | 7 | 9 | 10 | 9 | 4 | 3 | 8 | 0 |

EXAMPLE 4

Antidoting Activity of Compound III - Pot Test

Standard tests were made with addition of water-leakage conditions of 2 cm/24 hours for 3 days, using a wagner pot with 1/5000 are. Seedlings of 2.5 leaved Japonica rice plant NIHONBARE raised in a seedling growing box were transplanted into the pot. Chemical treatment was effected one day after transplantation in application rates indicated in Table 4. During the test season water depth was held at 3 mm at the above water-leaking conditions. Observations and investigations were made 15 days and 22 days after the chemical application and are reported in Table 4. Evaluations were made according to the scale described in Example 1.

TABLE 4

| Chemical | Application rate (g/ha) | Assessment (rice phytotoxicity) | | Rice Growth condition* (%) | | |
|---|---|---|---|---|---|---|
| | | After 15 days | After 20 days | Stalk number | Plant length | Dry weight of ground part |
| Compound I | 100 | 3.5 | 4 | 91 | 100 | 82 |
| Compound I + Compound III | 100 + 2000 | 1 | 1.5 | 98 | 102 | 95 |
| Compound III | 2000 | 0 | 0 | 108 | 99 | 110 |
| Control (untreated) | — | 0 | 0 | 100 | 100 | 100 |

*Indicated in percentages (%) based on the stalk number, plant length and dry weight of ground part in Control.

EXAMPLE 5

Antidoting Activity of Compound III - Field Test

Field tests under natural conditions were conducted in paddy fields in eight locations in Japan. Seedlings of Japonica rice plant, NIHONBARE, 2.2 to 2.5 of leaf age, were transplanted, respectively, by rice planter or by hand in paddy fields after breaking land, watering, fertilizing, plowing and leveling according to customary practice. After transplantation the surface water of the paddy field was held in condition where water was filled in a depth of 3 to 5 cm. The chemicals shown in Table 5 were applied to the water surface 10 days after transplantation. Testing was made in 7 m² for every area, respectively in the double system. Table 5 shows results of observations made 35-41 days after the chemical application. Results are indicated as average values (rounded off) of test results in the 8 different places. Assessment of phytotoxicity and herbicidal effect are the same as described in Examples 1 and 3.

TABLE 5

| Chemical | Application rate (g/ha) | Herbicidal Effect | | | | | | | | Phytotoxicity to rice |
|---|---|---|---|---|---|---|---|---|---|---|
| | | Annual field weeds | | | Perennial field weeds | | | | | |
| | | Ec | Mv | Bl | Ea | Sh | Sp | Ac | Cs | |
| Compound I | 75 | 5 | 10 | 10 | 10 | 9 | 9 | 8.5 | 9 | 3.5 |
| | 100 | 6 | 10 | 10 | 10 | 9.5 | 9.5 | 9 | 9 | 4.4 |
| Compound I + Compound III | 75 + 2100 | 9.5 | 10 | 9.5 | 10 | 9 | 9 | 9 | 9 | 0.5 |
| Compound I + Compound III | 100 + 4000 | 10 | 10 | 10 | 10 | 9.5 | 9 | 9.5 | 9 | 0.7 |
| Compound III | 2000 | 8 | 4 | 4 | 2 | 2 | 2 | 0 | 3 | 0 |
| | 4000 | 10 | 6 | 5 | 4 | 3 | 2 | 2 | 5 | 0 |

The method of this invention can be conveniently carried out by application of an herbicidal composition comprising Compound I and either Compound II or III as active ingredients. Such a composition can be formulated in any number of ways, for example, as a dust, particle, granule, tablet, suspending agent, emulsion, wettable powder, concentrated emulsion, or aerosol. The composition comprises a herbicidally effective amount of Compound I, an antidotally effective amount of Compound II or III and, optionally, one or more agriculturally suitable diluents.

Examples of agriculturally suitable adjuvants include but are not limited to solid or liquid carriers or diluents, such as kaolinite, attapulgite, montmorillonite, diatomaceous earth, bentonite, talc, pyrophyllite, calcined vermiculite, silica, magnesium silicate, ammonium sulfate, magnesium sulfate, calcium sulfate, disodium phosphate, starch, water, aliphatic hydrocarbon, aromatic hydrocarbon, alcohols, ethylene glycol, cellosolve, and methyl cellosolve; emulsions, dispersants and wetting agents, such as alkyl allyl sulfonate, alkyl sulfate, polyoxyethylene alkyl phosphate, polyoxyethylene lauryl ether, polyoxyethylene alkyl phenyl ether, polyoxyethylene sorbitan monolaurate, polyethylene glycol alkyl ether, polyoxyethylene alkyl phenyl ether, alkyl benzenesulfonate, and ligninsulfonate.

The content of the active ingredients in the composite composition can range from about 0.01 to 100 weight %, preferably about 0.1 to 90 weight %, of the composition.

Examples of herbicidal compositions according to this invention are presented below.

EXAMPLE 6

Wettable powder

Compound I and Compound II (weight ratio 1:28): 80% wt
Sodium alkyl naphthalenesulfonate: 2% wt
Sodium ligninsulfonate: 2% wt
Synthetic amorphous silica: 3% wt
Kaolinite: 13% wt These components are mixed, pulverized in a hammer mill in such a manner as to reach 5 microns or less in particle diameter and then remixed.

EXAMPLE 7

Wettable powder

Compound I and Compound II (weight ratio 1:25): 50% wt
Sodium alkyl naphthalenesulfonate: 2% wt
Methyl cellulose: 2% wt
Diatomaceous earth: 46% wt These components are mixed, roughly pulverized in a hammer mill, then pulverized in a size of 10 microns or less in diameter in an air mill and remixed.

EXAMPLE 8

Granule

Compound I and Compound II (weight ratio 1:28): 25% wt
Pregranulated bentonite base carrier: 75% wt A methylene chloride solution of Compound I and Compound II is supported on the surface of pregranulated particulate bentonite carrier by spraying and impregnating and dried naturally.

EXAMPLE 9

Extrusion granule

Compound I and Compound II (weight ratio 1:25): 25% wt
Anhydrous sodium sulfate: 10% wt
Calcium ligninsulfonate: 5% wt
Sodium alkylnapthalenesulfonate: 1% wt
Bentonite: 59% wt The respective components are mixed, pulverized in a hammer mill and kneaded together by addition of about 12% water. It is extruded through an extrusion granulator about 3 mm in diameter and cut off about 3 mm long to make granules.

EXAMPLE 10

Low concentrated granule

Compound I and Compound II (weight ratio 1:30): 1% wt
N-dimethylformamide: 9% wt
Attapulgite: 90% wt Active components are dissolved in solvent and sprayed over particles in a rotary mixer. After the spraying is finished, the mixer is run for some time.

EXAMPLE 11

Oily suspending agent

Compound I and Compound II (weight ratio 1:25): 25% wt
Polyoxyethylene sorbitol hexaoleate: 5% wt
Higher aliphatic hydrocarbon oil: 70% wt The respective components are pulverized in a sand mill to produce particles of about 5 micron or less. This product can be used by extending with oil or by emulsifying in water.

What is claimed is:

1. A method for controlling weeds in paddy fields of Japonica rice plants consisting essentially of applying to the locus of said weeds an herbicidally effective amount of the herbicidal compound methyl 2-[((4,6-dimethoxypyrimidin-2-yl)aminocarbonyl)aminosulfonyl]-methyl benzoate and an antidotally effective amount of an antidotal compound selected from S-(4-chlorobenzyl)N,N-diethylthiolcarbamate and S-(1-methyl-1-phenethyl)-piperidine-1-carbothioate.

2. The method of claim 1 where the antidotal compound is S-(4-chlorobenzyl)-N,N-diethylthiocarbamate.

3. The method of claim 1 where the antidotal compound is S-(1-methyl-1-phenethyl)-piperidine-1-carbothioate.

4. A method according to claim 1 where the herbicidal compound and the antidotal compound are applied to the water surface of the paddy field about one to fifteen days after the rice plants have been transplanted therein.

5. A method according to claim 2 where the herbicidal compound and the antidotal compound are applied to the water surface of the paddy field about one to fifteen days after the rice plants have been transplanted therein.

6. A method according to claim 3 where the herbicidal compound and the antidotal compound are applied to the water surface of the paddy field about one to fifteen days after the rice plants have been transplanted therein.

7. The method of claim 2 where the herbicidal compound and the antidotal compound are applied in a weight ratio of 1:20 to 1:50.

8. The method of claim 3 where the herbicidal compound and the antidotal compound are applied in a weight ratio of 1:10 to 1:50.

9. A herbicidal composition consisting essentially of a herbicidally effective amount of the herbicidal compound methyl 2-[((4,6-dimethoxypyrimidin-2-yl)aminocarbonyl)- aminosulfonyl]-methyl benzoate, an antidotally effective amount of an antidotal compound selected from S-(4-chlorobenzyl)-N,N-diethylthiocarbamate and S-(1-methyl-1-phenethyl)-piperidine-1-carbothioate, and one or more agriculturally suitable adjuvants.

10. The composition of claim 9 where the antidotal compound is S-(4-chlorobenzyl)-N,N-diethylthiocarbamate.

11. The composition of claim 9 where the antidotal compound is S-(1-methyl-1-phenethyl)-piperidine1-carbothioate.

12. The composition of claim 10 where the herbicidal compound and the antidotal compound are present in a weight ratio of 1:20 to 1:50.

13. The composition of claim 11 where the herbicidal compound and the antidotal compound are present in a weight ratio of 1:10 to 1:50.

* * * * *